United States Patent
Altundas et al.

(10) Patent No.: US 10,101,255 B2
(45) Date of Patent: Oct. 16, 2018

(54) APPARATUS AND METHODS FOR ANALYSIS OF RESERVOIR FLUIDS

(71) Applicant: SCHLUMBERGER TECHNOLOGY CORPORATION, Sugar Land, TX (US)

(72) Inventors: Yusuf Bilgin Altundas, Burlington, MA (US); Chaur-Jian Hsu, Danbury, CT (US); Terizhandur S. Ramakrishnan, Boxborough, MA (US); Quincy K. Elias, Mattapan, MA (US); Albert Perez, Jr., Brookfield, CT (US)

(73) Assignee: SCHLUMBERGER TECHNOLOGY CORPORATION, Sugar Land, TX (US)

(*) Notice: Subject to any disclaimer, the term of this patent is extended or adjusted under 35 U.S.C. 154(b) by 295 days.

(21) Appl. No.: 14/851,561

(22) Filed: Sep. 11, 2015

(65) Prior Publication Data

US 2017/0074096 A1 Mar. 16, 2017

(51) Int. Cl.
| | |
|---|---|
| *G01V 1/00* | (2006.01) |
| *G01N 9/00* | (2006.01) |
| *E21B 49/08* | (2006.01) |
| *G01N 11/00* | (2006.01) |
| *G01N 33/28* | (2006.01) |
| *G06F 11/30* | (2006.01) |

(52) U.S. Cl.
CPC ............ *G01N 9/00* (2013.01); *E21B 49/082* (2013.01); *G01N 11/00* (2013.01); *G01N 33/28* (2013.01); *E21B 2049/085* (2013.01); *G01N 2203/0085* (2013.01)

(58) Field of Classification Search
CPC ........................................................ G01N 9/00
See application file for complete search history.

(56) References Cited

U.S. PATENT DOCUMENTS

| | | |
|---|---|---|
| 4,994,671 A | 2/1991 | Safinya et al. |
| 5,167,149 A | 12/1992 | Mullins et al. |
| 5,201,220 A | 4/1993 | Mullins et al. |
| 5,266,800 A | 11/1993 | Mullins |
| 5,331,156 A | 7/1994 | Hines et al. |
| 5,859,430 A | 1/1999 | Mullins et al. |
| 6,378,364 B1 | 4/2002 | Pelletier et al. |
| 6,474,152 B1 | 11/2002 | Mullins et al. |
| 6,640,625 B1 | 11/2003 | Goodwin |
| 7,913,556 B2 | 3/2011 | Hsu et al. |
| 7,921,691 B2 | 4/2011 | DiFoggio et al. |
| 8,321,133 B2 | 11/2012 | Hsu et al. |

(Continued)

OTHER PUBLICATIONS

Besson, R. J. et al., "A Dual-Mode Thickness-Shear Quartz Pressure Sensor", IEEE Transactions on Ultrasonic, Ferroelectrics and Frequency Control, 1993, 40(5), 8 pages.

(Continued)

*Primary Examiner* — Phuong Huynh

(57) ABSTRACT

Methods and apparatus are provided for the measurement of the compressibility of reservoir fluid. A piezoelectric material is coupled to a wall of a fluid chamber. Compressibility is derived from measured pressure changes to the fluid resulting from volumetric changes to the fluid chamber imposed by the mechanical strain of the piezoelectric material resulting from an applied electric field.

20 Claims, 4 Drawing Sheets

(56) References Cited

U.S. PATENT DOCUMENTS

| 8,612,154 | B2 | 12/2013 | Hsu | |
|---|---|---|---|---|
| 2002/0113717 | A1* | 8/2002 | Tang | G01V 1/44 340/854.4 |
| 2012/0037423 | A1* | 2/2012 | Geerits | E21B 47/00 175/50 |

OTHER PUBLICATIONS

Cain, M. G. et al., "Degradation of Piezoelectric Materials", National Physical Laboratory Management Ltd., 1999, 41 pages.
Liang, L. et al., "Pressure and Electric Field Effects of Piezoelectric Responses of KNb03" Journal of Applied Physics, 2012, 112, 6 pages.
Matsumoto, N. et al., "Long-Term Stability and Performance Characteristics of Crystal Quartz Guage at High Pressures and Temperatures", IEEE Transactions on Ultrasonic, Ferroelectrics and Frequency Control, 2000, 47(2), 9 pages.
Nishi, R. Y. et al., "Behavior of Plezoceramic Projector Materials Under Hydrostatic Pressure", Journal of the Acoustical Society of America, 1964 36(7), pp. 1292-1296.

\* cited by examiner

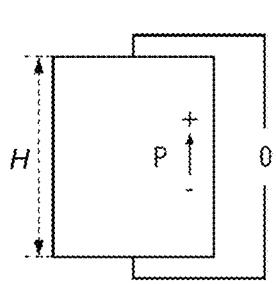 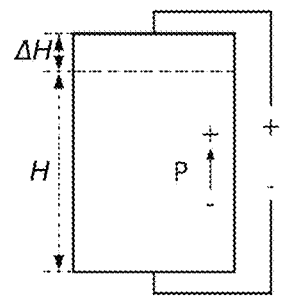 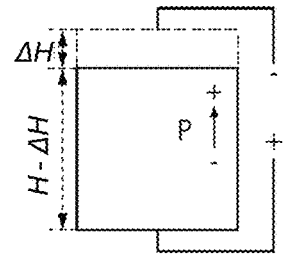
FIG. 3A              FIG. 3B              FIG. 3C
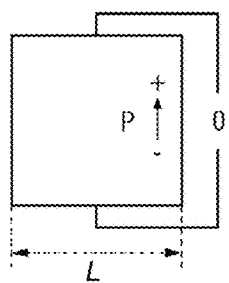 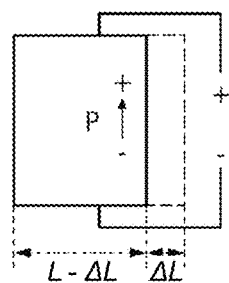 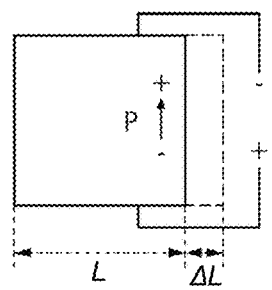
FIG. 4A              FIG. 4B              FIG. 4C
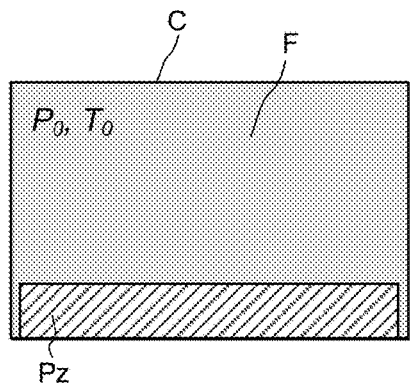 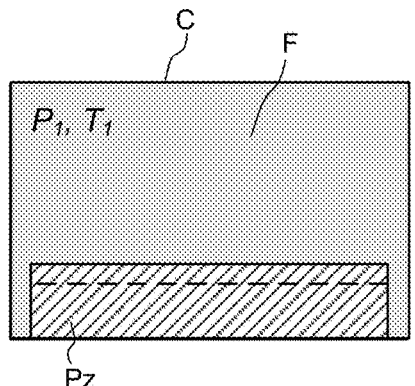
FIG. 5A              FIG. 5B

APPARATUS AND METHODS FOR ANALYSIS OF RESERVOIR FLUIDS

TECHNICAL FIELD

The subject disclosure relates to the investigation of formation fluids. More particularly, the subject disclosure relates to apparatus and methods for identifying downhole the characteristics of a formation fluid such as, e.g., the fluid compressibility and fluid bulk density of the formation fluid.

BACKGROUND

It has long been desirable to characterize fluids in a geological formation. For example, in interpreting wellbore monitoring measurements and seismic surveys for phase saturation, the thermodynamic properties of the multicomponent reservoir fluid are required, because the acoustic velocity of the fluid is determined by both the density and the isentropic compressibility, and both velocity and density are needed to decipher seismic data. Thus, it may be inferred that density and isentropic compressibility are fundamental for seismic interpretation. Correspondingly, isothermal fluid compressibility is required for well-test interpretation. In formation testing, early transients are strongly influenced by the fluid within the tool, and interpretation of data requires tool-fluid compressibility. Despite the desirability of obtaining in situ measurements of compressibility of nearly incompressible fluids, such measurements have been generally unavailable. Rather, for measuring compressibility, practice is to bring reservoir fluid samples to the surface laboratory.

When reservoir fluid samples are brought to the surface, pressure and/or temperature changes during the transfer can lead to undesirable component separations and potentially irreversible alterations of the fluid. While gas evolution may be reversed, asphaltene separation from crude oil is generally not reversible within reasonable time-scales. As a result, the results of surface measurements on the fluid can have large uncertainties, even when the fluid is reconstituted.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

Methods and apparatus are provided for in situ measurement of compressibility of reservoir fluid. The apparatus and methods derive compressibility from volumetric changes imposed by mechanical strain of a piezoelectric material induced by an applied electric field.

In some embodiments, a downhole tool is provided with a chamber that is arranged to receive formation fluids and either contains or has a wall coupled to a piezoelectric material. A pressure sensor that measures the pressure in the chamber is provided. Fluid that is to be investigated is provided to the chamber, and a voltage is applied to the piezoelectric material in order to alter the shape of the piezoelectric material and thereby change the volume of the chamber. A change in fluid pressure is measured by the pressure sensor, and the change in pressure is used in conjunction with a known change in chamber volume to derive compressibility.

In some embodiments, the piezoelectric material is located completely inside the fluid chamber. When a voltage is applied to the piezoelectric material, the piezoelectric material contracts in directions orthogonal to poling directions, but expands along its vertical poling direction, thereby changing its volume. The change in bulk volume of the piezoelectric material thereby changes the remaining volume in the chamber for the fluid. The change in pressure resulting from the change in bulk volume (or the change in fluid volume) is then related to the compressibility of the fluid.

In some embodiments, where the change in the fluid volume in the chamber is impacted by change in the volume of the piezelectric material resulting from change in the dimension of the material in multiple directions, the relationship between the change in pressure and the fluid compressibility is expressed according to $$\Delta P = \frac{\alpha(2d_{31} + d_{33})E_3}{\beta_T} \quad (1)$$

where $\Delta P$ is the change in pressure, $\alpha$ is the volume ratio between the fluid and the piezoelectric material, $d_{31}$ and $d_{33}$ are the respective tensor components of piezoelectric moduli of the piezoelectric material in the directions orthogonal and parallel to the poling direction, respectively, $E_3$ is a measure of the applied electrical field along the poling direction, and $\beta_T$ is the isothermal fluid compressibility.

In another embodiment, the piezoelectric material is located either outside the fluid chamber and is coupled to a wall of the fluid chamber, or a diaphragm is located in the chamber, and the piezoelectric material is separated from the fluid in the chamber by the diaphragm. When a voltage is applied to the piezoelectric material, the material moves the diaphragm or a wall of the chamber, thereby changing the volume of the chamber (or portion of the chamber containing the fluid) and hence the volume of the fluid. The change in pressure resulting from the change in in fluid volume is then be related to the compressibility of the fluid.

In some embodiments, where the fluid volume in the chamber is changed by movement of a chamber wall or a diaphragm resulting from application of a voltage to a piezoelectric material, the relationship between the change in pressure and the fluid compressibility can be expressed according to $$\Delta P = \frac{d_{33}E_3 A l_p}{V_f \beta_T} \quad (2)$$

where A is the cross-sectional area of the chamber, $l_p$ is the height (thickness) of the piezoelectric material prior to activation, and $V_f$ is the fluid volume.

In some embodiments, a sound speed sensor is also provided. The sound speed sensor may include a sonic transmitter and receiver that are coupled to a wall or to walls of the chamber. Using a sound speed measurement made by the sound speed sensor and the compressibility as determined resulting from the volume change in the chamber and the resulting pressure change, other characteristics of the fluid such as the bulk density or the specific heat ratio may be inferred.

Additional aspects, embodiments, objects and advantages of the disclosed methods may be understood with reference to the following detailed description taken in conjunction with the provided drawings.

BRIEF DESCRIPTION OF THE DRAWINGS

FIGS. 3a-3c are schematics of the longitudinal converse piezoelecctric effect in a body of piezoelectric ceramic where no electrical field is applied, where the applied electrical field has the same polarity as the poling voltage respectively, and where the applied electrical field has the opposite polarity as the poling voltage.

FIGS. 4a-4c are schematics of the transverse converse piezoelecctric effect in a body of piezoelectric ceramic where no electrical field is applied, where the applied electrical field has the same polarity as the poling voltage respectively, and where the applied electrical field has the opposite polarity as the poling voltage.

FIGS. 5a and 5b are respectively schematics showing a piezoelectric material in a fluid chamber with no electrical field applied, and with an electrical field applied resulting in an expansion of the piezoelectrical material and a compression of the fluid in the fluid chamber.

DETAILED DESCRIPTION

The particulars shown herein are by way of example and for purposes of illustrative discussion of the examples of the subject disclosure only and are presented in the cause of providing what is believed to be the most useful and readily understood description of the principles and conceptual aspects of the subject disclosure. In this regard, no attempt is made to show details in more detail than is necessary, the description taken with the drawings making apparent to those skilled in the art how the several forms of the subject disclosure may be embodied in practice. Furthermore, like reference numbers and designations in the various drawings indicate like elements.

Figure 1:
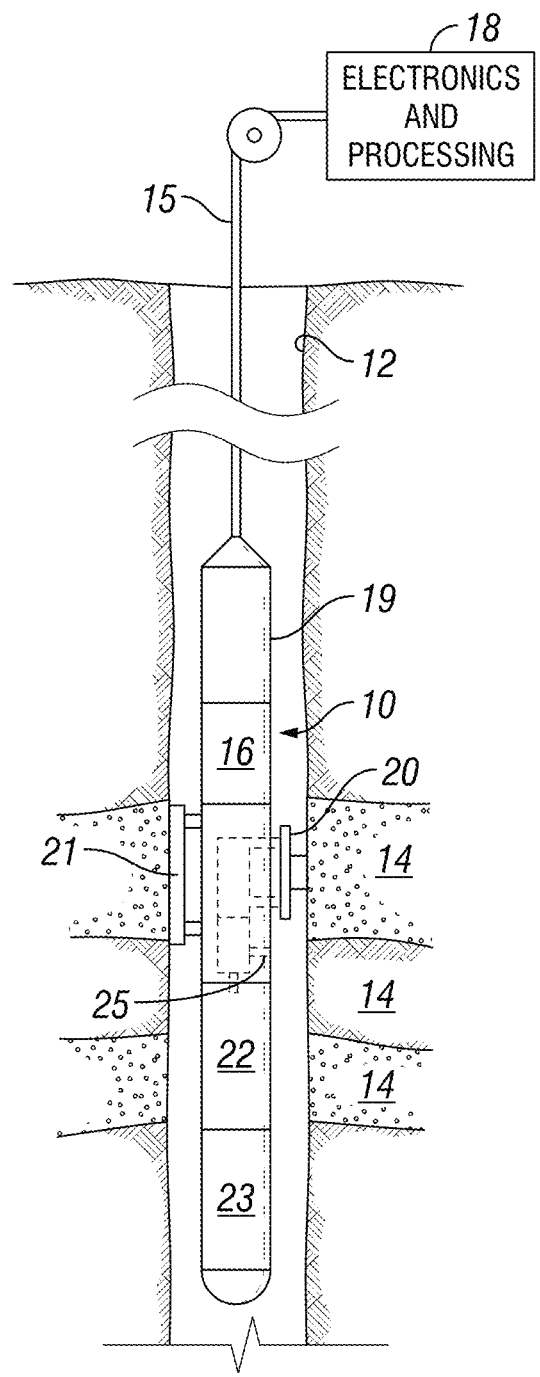
FIG. 1 is a schematic of a tool located in a borehole traversing a formation.

Turning to FIG. 1, a tool 10 for testing earth formations and analyzing the composition of fluid (e.g., oil) from the formation 14 is seen. Tool 10 is suspended in a borehole (or wellbore—the two being used interchangeably herein) 12 from the lower end of a typical multiconductor cable 15 that is spooled in a usual fashion on a suitable winch (not shown) on the formation surface. On the surface, the cable 15 may be electrically coupled to an electrical control system 18 which may include a processor as described in more detail hereinafter. The tool includes an elongated body 19 which encloses the downhole portion of the tool control system 16. The elongated body 19 also carries a selectively extendable fluid admitting assembly 20 and a selectively extendable tool anchoring member 21 which are respectively arranged on opposite sides of the body. The fluid admitting assembly 20 is equipped for selectively sealing off or isolating selected portions of the wall of the borehole 12 such that pressure or fluid communication with the adjacent earth formation is established. Also included with tool 10 is an optional fluid analysis module 25 through which the obtained fluid can flow. The fluid may thereafter be expelled through a port (not shown) or may be sent to one or more fluid collecting chambers 22 and 23 which may receive and retain the fluids obtained from the formation. Where a fluid analysis module is provided, the fluid analysis module may include an optical fluid analyzer such as shown and described in U.S. Pat. No. 4,994,671 to Safinya et al., U.S. Pat. No. 5,167,149 to Mullins et al., U.S. Pat. No. 5,201,220 to Mullins et al., U.S. Pat. No. 5,266,800 to Mullins et al., U.S. Pat. No. 5,331,156 to Hines et al., U.S. Pat. No. 5,859,430 to Mullins et al., all of which are hereby incorporated by reference herein in their entireties.

Figure 2:
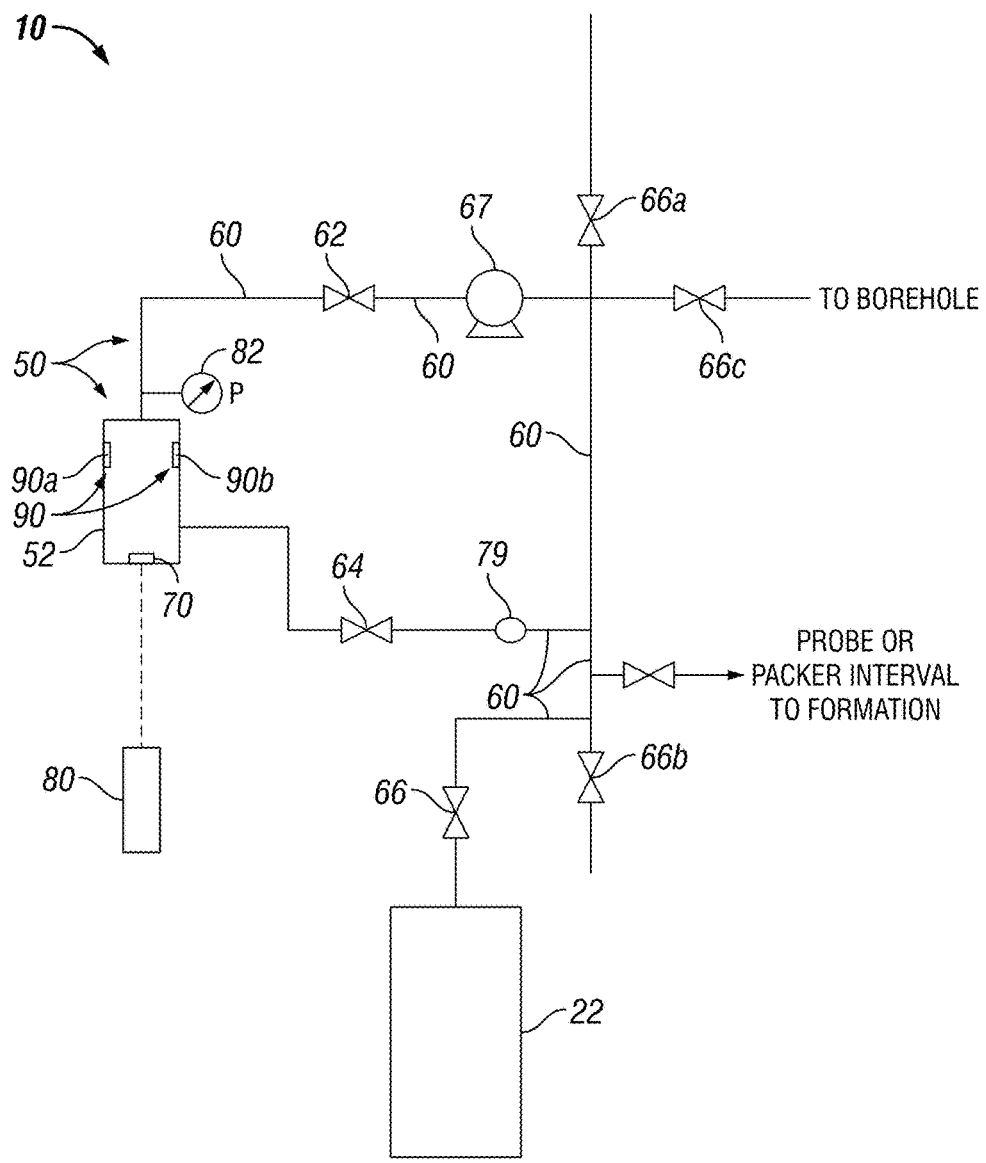
FIG. 2 is a schematic of a portion of the tool of FIG. 1 used in determining formation fluid compressibility.
Figure 6A:
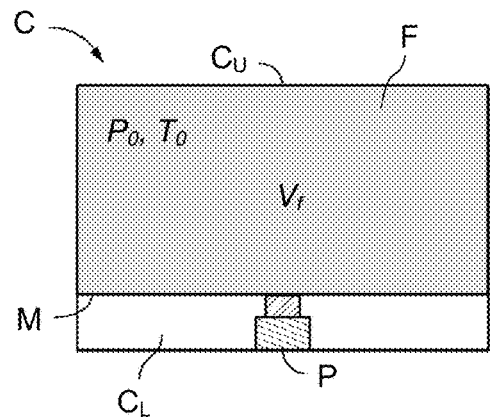
FIGS. 6a and 6b are respectively schematics showing a piezoelectric material in contact with a diaphragm in a chamber with no electrical field applied, and with an electrical field applied resulting in a decrease in the fluid volume of the chamber.
Figure 6B:
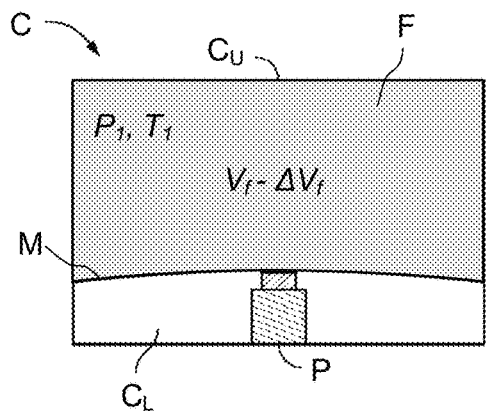
Figure 7A:
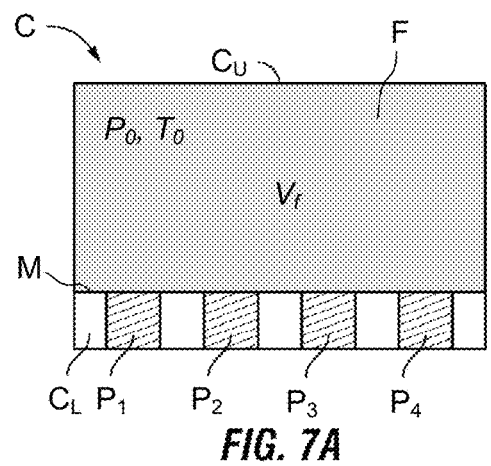
FIGS. 7a and 7b are respectively schematics showing piezoelectric materials in contact with a diaphragm in a chamber with no electrical field applied, and with an electrical field applied resulting in a decrease in the fluid volume of the chamber.
Figure 7B:
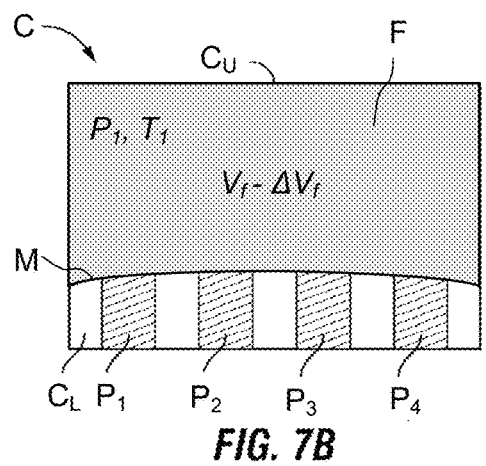

As shown in FIG. 2, the tool 10 includes a fluid compressibility analysis module 50 which may be a separate module or may be part of or share elements of the fluid analysis module 25. The fluid compressibility analysis module 50 may be under control of up-hole electronics and processing unit 18 as described in more detail hereinafter. In some embodiments, the fluid compressibility analysis module 50 is provided with a chamber 52 coupled by pipes or tubes 60 to a source of formation fluid via a valve 62. Other valves such as valves 64 and 66 may also be provided to control fluid flow. A pump 67 may be used to cause the formation fluid to be provided directly from the formation or from a storage chamber such as a fluid collecting chamber 22 that may be kept at or near formation pressures. As will be described in more detail hereinafter with respect to FIGS. 5-7, in some embodiments, the chamber 52 contains therein a piezoelectric material 70. The piezoelectric material is coupled (e.g., via wires that extend through a chamber wall), to a voltage source 80 which, in some embodiments is located in the tool control module 16. In another embodiment, the chamber has a diaphragm (e.g., membrane or wall) which separates the chamber into a portion containing fluid and a portion that does not contain fluid, and the piezoelectric material 70 is coupled to a side of the diaphragm that is not in contact with the fluid in the chamber. Again, the piezoelectric material 70 is coupled to a voltage source 80 located in the tool control module 16 or elsewhere. In some embodiments, the piezoelectric material 70 is coupled to a chamber wall and to a voltage source 80. A pressure sensor 82 is coupled to the chamber 52 to measure the fluid pressure of the chamber 52. In some embodiments, the pressure sensor 82 is located internal to the chamber 52.

In some embodiments, valve 64 is opened, the pump 67 is activated, and valve 62 is opened in order to allow fluid from the formation (or optionally fluid stored in chamber 22 or another chamber) to enter the chamber 50, typically at or close to downhole formation (ambient) pressure and be flushed via valve 66c that is opened to the borehole. When satisfactory collection of the native formation fluid is obtained, valves 66c and 62 may be shut. With the pressure sensor 82 sensing that a desired pressure has been obtained, pump 67 is shut and valve 64 is shut, thereby establishing a closed system in chamber 52. In situations, such as in FIG. 2, where valves are spaced apart from the chamber 52, the closed system also includes any volume of fluid in the pipes or tubes 60 that is in fluid and pressure communication with the fluid in chamber 52 when the valves 62 and 64 are closed. In such cases, this volume of fluid in the pipes or tubes 60 may be considered part of the volume of the chamber 52 at least for purposes of analyzing the closed system.

A voltage is then applied by voltage source 80 to the piezoelectric material 70 to alter the shape of the material 70 and to cause a change in the fluid-containing volume of the chamber as described in more detail hereinafter. An indication of the pressure (i.e., the pressure or pressure change) of the fluid-containing volume of the chamber is then measured, and the pressure change is used by the electronics and processing block 18 to find an indication of the compressibility of the fluid in the chamber as described in more detail hereinafter.

In the illustrated examples, the walls of the fluid chamber (and relevant portions of pipes/tubes 60) are substantially rigid, except to the extent of walls, membranes, or other surfaces that are selectably deformable for the purpose of controllably reducing the volume of the chamber 52 as described herein. It should be understood, however, that other examples may have other walls that may not be substantially rigid, e.g., where a wall is flexible or non-rigid in a manner that may be accounted for in calculating the compressibility.

In some embodiments, the chamber 52 is also provided with a sound speed (velocity) sensor 90, which may include a sonic wave transmitter 90a and a receiver 90b that may be coupled to one or more walls of the chamber. Using a sound speed measurement made by the sound speed sensor 90 and the compressibility as determined, characteristics of the fluid such as bulk density or specific heat ratio may be inferred by the processing block 18 as described in more detail hereinafter.

In some embodiments, once an experiment has been conducted down-hole to find the compressibility of a fluid sample, valve 66 may be opened to cause the fluid in the chamber to be jettisoned from the module or stored in a desired location, or valve 66c may be opened to eject the stored fluid into the borehole so as to be replaced by a second fluid. Thus, the module 50 may then be utilized to conduct additional experiments with a different fluid samples obtained at the same or a different location in the borehole.

In one aspect, isothermal compressibility $\beta_T$ is defined as $$\beta_T = -\frac{1}{V}\frac{\partial V}{\partial P} \quad (3)$$

where V(P,T) is the molar volume and P and T are the fluid pressure and temperature, respectively. For a finite fluid volume change $\Delta V$, and the corresponding change in fluid pressure $\Delta P$, isothermal compressibility of the corresponding fluid may be calculated from $$\beta_T \approx -\frac{1}{V}\frac{\Delta V}{\Delta P}. \quad (4)$$

Since $\beta_T$ varies with P and T, according to some embodiments, $\Delta P/P \ll 1$; e.g., $\Delta P/P$ is less than $1/100$.

In one aspect, piezoelectric materials, when deformed, develop dipoles within the solid and cause a resulting charge accumulation on surface electrodes. The developed electric displacement or charge density is proportional to the imposed mechanical stress. Conversely, in an electric field, a piezoelectric material (e.g., crystal) experiences a volumetric strain. This strain is well characterized, and as set forth hereinafter, it is this volumetric strain that is utilized to change the volume of the fluid chamber 52.

Many practical piezo-materials are polycrystalline ceramics, examples of which include lead zirconate, lead titanate, and barium titanate. Although they are apparently piezoelectric, they are polarized electrostrictive, i.e., polycrystalline materials are subjected to a poling DC potential across the material so as to exhibit piezoelectricity through grain alignment. The material undergoes a semi-permanent dimensional increase in the poling direction. A dimensional decrease occurs in the orthogonal directions.

For post-poling deformations, if the applied voltage has the same polarity as the poling voltage, the material expands parallel to the applied electric field (as seen by comparing FIG. 3b with FIG. 3a where no voltage is applied), and shrinks transverse to it (as seen by comparing FIG. 4b with FIG. 4a where no voltage is applied). Conversely, if the voltage has the opposite polarity, the material shortens parallel to the field (as seen by comparing FIG. 3c with FIG. 3a) and lengthens transversely (as seen by comparing FIG. 4c with FIG. 4a).

In some embodiments, the tendency of the piezoelectric materials to expand or shrink is utilized for the purpose of changing the volume of the fluid chamber 52. In some embodiments, the ceramic material may be well-characterized for its deformation behavior. In particular, the piezoelectric material is strained by applying an electric voltage which results in an increase in pressure in the confined fluid. The change in pressure $\Delta P$ is easily calculated from the known converse piezoelectric effect through the constitutive relationship of the ceramic. In particular, $\Delta P$ is easily calculated from the volume of the fluid ($V_f$), the change in $V_f$, ($\Delta V_f = -\Delta V_p$ when fluid surrounds the piezoelectric material), and the temperature, provided the consequential pressure induced volume strain on the piezo-electric material is shown to be small. Since any alteration in pressure resists deformation, in some embodiments, a perturbation series is considered.

Piezoceramic (as opposed to soft piezopolymers) materials generally have bulk moduli of between 10 and 100 GPa and density of between 7000 and 8000 kg m$^{-3}$. The expected piezoelectric moduli for ceramics have magnitudes of about $4 \times 10^{-10}$ m V$^{-1}$. The strain transverse to the imposed field is nearly one-half and therefore the volumetric strain is rather small, about one-tenth of the longitudinal strain. For electric fields of about 400 kV m$^{-1}$, it is reasonable to expect a pressure deflection of 780 Pa or more for an arrangement having a 1:100 volume ratio of piezoceramic to aqueous fluid. The sensitivity may be improved with smaller fluid chambers.

In general, piezoelectric materials can produce strains in the range of 0.01% to 0.2% for hard materials and 10 to 100% for soft materials, thus exhibiting a bulk volume change in enclosed media.

While soft piezoelectric materials would provide a higher strain than hard ones, ceramics show no detectable degradation and are resilient to cyclic loading. In one aspect, any of many ceramic materials may be utilized, including, by way of example and not by way of limitation, a number of naturally occurring materials such as quartz, tourmaline, sodium potassium tartarate and Rochelle salts, and a number of synthetic piezoceramic materials such as PZT (Lead Zirconium Titanate) and PT (Lead Titanate). Materials such as PZT (Pb(Zr, Ti)O$_3$, PT (Pb TiO$_3$) and PLZT (Pb La)(Zr Ti)O$_3$) may be manufactured with properties such that their physical, chemical and piezoelectric characteristics may be adapted for desired purposes, i.e, suitable shapes, size, with choice of axes and orientation.

The relation between the applied electric field strength and the resulting strain in a piezoceramic material is given by $$\varepsilon_j = S_{ij}\sigma_j + d_{ij}E_i, \quad i,j = 1,2,3 \quad (5)$$

where i and j are the cartesian indices, $d_{ij}$ are tensor components of the piezoelectric moduli, $E_i$ is the applied electrical field, and $\sigma_j$ and $S_{ij}$ are the stress and compliance of the material respectively. Piezoelectric moduli tensor component values for an example of both a soft and a hard piezoelectric material are given in Table 1.

TABLE 1

| Material | $d_{33}$ | $d_{31}$ |
|---|---|---|
| Hard PZT | 350-650 pmV$^{-1}$ | (−)320-150 pmV$^{-1}$ |
| Soft PZT | 600 pmV$^{-1}$ | (−)275 pmV$^{-1}$ |

Bulk moduli of piezo-ceramic materials are quite high, in excess of (100 GPa), making the material quite incompressible compared to fluids. Therefore, eq. (5) may be rewritten as $$\varepsilon_j \approx d_{ij} E_i \quad (6)$$

For a vertical poling direction (z-axis) on a piezoceramic disk, displacements due to piezoelectric effect are given by $$\Delta R = R d_{31} E_3 \quad (7)$$

$$\Delta l_p = l_p d_{33} E_3 \quad (8)$$

where R and $l_p$ are respectively the radius and the thickness of the piezo-ceramic disk, and $E_3 = V_{dr}/l_p$ where $V_{dr}$ is the drive voltage applied to the piezo-ceramic. It should be appreciated that $d_{31}$ is a negative quantity (close to $d_{33}/2$ in magnitude) and, therefore, represents a radial contraction, i.e., orthogonal to the poling direction. Thus, as suggested by comparing FIGS. 5a and 5b where a piezo-ceramic material P is immersed in fluid F within a chamber C, while the piezo-ceramic material P expands in a poling direction (as discussed with reference to FIG. 3b) thereby tending to reduce the fluid volume remaining in the fixed-volume chamber, the same material contracts in the direction perpendicular to the poling direction (as discussed with reference to FIG. 4b), thereby tending to increase the fluid volume remaining. The contraction effectively reduces the negative change in fluid volume. The change in the bulk volume is then described according to $$\Delta V_p = -\Delta V_f \approx \left[ \frac{2\Delta R}{R} + \frac{\Delta l_p}{l_p} \right] \pi R^2 l_p = [2d_{31} + d_{33}] E_3 \pi R^2 l_p. \quad (9)$$

Equation (9) can be reduced to $$\Delta V_f = -[2d_{31} + d_{33}] E_3 V_p \quad (10)$$

where the volume of piezoceramic disk $V_p = \pi R^2 l_p$.

In one aspect, the characteristic numbers for a specific piezoceramic crystal (ceramic APC 855(Navy VI)) subject to an electric field of 40 kV m$^{-1}$ may be derived. Consider a 1 cm$^3$ ceramic APC 855 crystal. For $l_p$=1 cm, R=$1/\pi^{0.5}$ cm. The piezoelectric moduli for the ceramic APC 855 are given as $d_{33}$=630×10$^{-12}$ m V$^{-1}$, and $d_{31}$=−276×10$^{-12}$ m V$^{-1}$. The APC 855 piezo-ceramic disk undergoes an extension of h=2.52×10$^{-4}$ mm and a contraction of R=−6.23×10$^{-5}$ mm under the specified 40 kV m$^{-1}$ electrical field. A corresponding volumetric change in the disk (which is the same magnitude as the displaced fluid) is about 3.12×10$^{-3}$ mm$^3$. In some embodiments, it is possible to amplify this volumetric change, by having the ceramic deflect a metallic membrane or wall, as described hereinafter. Also, since the change in fluid volume $\Delta V_f$ is proportional to the electrical field applied, increasing the electrical field will result in a larger volume change.

The difference in fluid pressure corresponding to fluid volume displaced in closed chamber can be calculated by using the equation $$\Delta P = -\frac{1}{V_f} \frac{\Delta V_f}{\beta_T} \quad (11)$$

where $\beta_T$ is the isothermal compressibility of the fluid. For in situ conditions, the temperature change $\Delta T$ resulting from the converse piezoelectric effect is negligible. Furthermore, since this measurement can be made very rapidly and the response is essentially instantaneous, setting $V_p = \alpha V_f$ for $\alpha \in R$ and substituting equation (10) into equation (11), the expression for change in pressure becomes $$\Delta P = \frac{\alpha(2d_{31} + d_{33}) E_3}{\beta_T}. \quad (12)$$

Thus, a volume ratio of 100:1 ($\alpha$=1/100) between the fluid and the piezo-ceramic results in a fluid volume strain of −3.12× 10$^{-8}$. For water, this results in a pressure increase of about 78 Pa under isothermal conditions. A more than one hundred times increase in $\Delta P$ is possible by increasing the volume ratio and the electric field (to, e.g., a maximum of about 1 kV mm$^{-1}$), and amplifying the displacement by utilizing the expansion of the disk in the poling direction only, e.g., deflecting a metallic membrane through the strain of the disk in poling direction. Hence, a 78-7800 Pa pressure increase through converse piezoelectric effect is attainable, a quantity which is certainly within pressure measurement capability. For example, it is known that Crystal Quartz Gauge (CQG) sensors for downhole pressure measurements yield a maximum 6.89 kPa+0.01% of reading error in static measurements and have resolutions better than 20.7 Pa. (See, R. J. Besson, et al., "A dual-mode thickness-shear quartz pressure sensor", IEEE Transactions on Ultrasonic, Ferroelectrics and Frequency Control, 40(5), 1993, and N. Matsumoto, et al., "Long-term stability and performance characteristics of crystal quartz gauge at high pressures and temperatures", IEEE Transactions on Ultrasonic, Ferroelectrics and Frequency Control, 47(2), 2000)). Moreover, the 0.01% of reading error is associated with the uncertainty in static pressure and will not contribute to a pressure difference measurement. With a fluid whose compressibility is about a factor ten more than water, pressure differences are lowered by a factor of ten, a quantity whose low end is just measurable at pressures of interest, but whose high end is easily measurable. Table 2 shows attainable pressure increases in water and oil through the converse piezoelectric effect for a range of ceramic-to-fluid volume ratios (e.g., 1%, 2%, 3%, 4%, 5%, 10% and 15%) and different electrical fields (e.g., 40 Vmm$^{-1}$, 50 Vmm$^{-1}$, 100 Vmm$^{-1}$ and 1000 Vmm$^{-1}$), where compressibility $\beta_T$ was set to equal 4.0×10$^{-10}$ Pa$^{-1}$ for water and 1.0×10$^{-9}$ Pa$^{-1}$ for oil.

TABLE 2

| $V_p/V_f$ [%] | $E_3$ [kV m$^{-1}$] | $\Delta P_w$ [Pa] | $\Delta P_o$ [Pa] |
|---|---|---|---|
| 1 | 40 | 78 | 31 |
| 1 | 50 | 95 | 39 |
| 2 | 50 | 195 | 78 |
| 3 | 50 | 293 | 117 |
| 4 | 50 | 390 | 156 |
| 5 | 50 | 488 | 195 |
| 10 | 50 | 975 | 390 |
| 1 | 100 | 195 | 78 |
| 2 | 100 | 390 | 156 |
| 3 | 100 | 585 | 234 |
| 4 | 100 | 780 | 312 |
| 5 | 100 | 975 | 390 |
| 10 | 100 | 1950 | 780 |
| 1 | 1000 | 1950 | 780 |
| 2 | 1000 | 3900 | 1560 |
| 3 | 1000 | 5850 | 2340 |
| 4 | 1000 | 7800 | 3120 |
| 5 | 1000 | 9750 | 3900 |
| 10 | 1000 | 19500 | 7800 |
| 15 | 1000 | 29250 | 11700 |

According to some embodiments, the compressibility of a fluid may be determined by providing the fluid to a chamber containing a piezoelectric material, applying a voltage to the piezoelectric material in order to alter the shape of the piezoelectric material, measuring a change in fluid pressure in the chamber, and using a processor (e.g., processing unit 18) to calculate the compressibility of the fluid according to equation (12), where the volume ratio of piezoelectric material to fluid ($\alpha$), the piezoelectric modulii $d_{31}$ and $d_{33}$, and the drive voltage parameter $E_3 = V_{dr}/l_p$ are known. In some embodiments, the compressibility of the fluid is determined with the fluid being analyzed downhole. In some embodiments, the compressibility of the fluid is determined using an apparatus such as described above with respect to FIGS. 1, 2, and 5. In some embodiments, the fluid is a hydrocarbon-containing fluid. In some embodiments, an indication of the compressibility of the fluid is provided on a log that shows the compressibility as a function of location (e.g., depth) in a formation at which the sample was obtained. The log may be provided and displayed on a computer or other electronic monitor, or may be provided and displayed on a tangible medium such as paper. In some embodiments, compressibility determinations are made for different samples of fluid obtained at different locations downhole, and a log of the fluid compressibility as a function of depth (i.e., different fluid samples located at different depths of the formation) may be provided and displayed.

As previously mentioned, net fluid volume displaced by the ceramic piezoelectric element due to the piezoelectric effect is affected by the shrinkage of the element in the direction orthogonal to the poling direction. This is especially true when $|d_{31}| \approx d_{33}/2$, which would make the net fluid volume displaced almost zero, as is evident from equation (12).

According to one aspect, the change in net fluid volume $\Delta V_f$ may be amplified by reconfiguring the system such that only the expansion of the piezoelectric element (in the poling direction) is utilized for the compression of the fluid and any contribution from $d_{31}$ is avoided. For instance, rather than submerging the piezoelectric element 70 fully into the fluid F as in FIGS. 5a and 5b such that the element 70 expands in one direction and contracts in another in the fluid, when voltage is applied to it as seen in FIG. 5b, the element may be separated from the fluid by a metallic membrane M as seen in FIGS. 6a, 6b and 7a, 7b, with the element on one side of the membrane and the fluid on the other side such that only the expansion of the element impacts the volume of the fluid. In particular, in the embodiments of FIGS. 6a, 6b, and 7a, 7b, the membrane M is attached, e.g., via welding, to the wall(s) of the chamber C, thereby creating an upper chamber $C_U$ containing the fluid F, and a lower chamber $C_L$ in which the piezoelectric element P is located in FIGS. 6a and 6b, and in which multiple piezoelectric elements $P_1$-$P_4$ are located in FIGS. 7a and 7b. As seen in FIGS. 6a, 6b, 7a, 7b, the piezoelectric element(s) P are arranged such they are coupled to both a fixed wall of the chamber and the membrane M of the chamber. The membrane M and the piezoelectric element(s) P are oriented to have the poling end of the element(s) P and the 70 membrane M aligned in the same plane. Thus, the strain due to $d_{33}$ on the ceramic element is fully utilized to displace the metallic membrane M in FIGS. 6b and 7b, thereby compressing the fluid F (i.e., reducing the fluid volume from $V_f$ to $V_f - \Delta V_f$).

According to one aspect, fluid displacement may be achieved either through deflecting a membrane or pushing a plate (not shown) or a wall of the chamber to compress the fluid while making sure that fluid mass inside chamber is conserved. For example, if it is assumed that a plate or membrane sits between fluid and one or more piezoceramic disk, then ignoring the bending of the membrane or plate (this can accounted for in detailed mechanical calculation) the volume change in fluid and the corresponding pressure change will be $$\Delta V_f = d_{33} E_3 A l_p \quad (13)$$

where A is the cross sectional area of the chamber and $l_p$ is the thickness, or height, of the crystal. Therefore, $$\Delta P = \frac{d_{33} E_3 A l_p}{V_f \beta_T}. \quad (14)$$

In this case, a substantially amplified pressure increase is obtained compared to the case of equation (12) when both $d_{33}$ and $d_{31}$ affect the resulting pressure change.

According to some embodiments, the compressibility of a fluid may be determined by providing the fluid to a chamber with a membrane or other element that is coupled to a piezoelectric material, applying a voltage to the piezoelectric material in order to alter the shape of the piezoelectric material, measuring a change in fluid pressure in the chamber, and using a processor to calculate the compressibility of the fluid according to equation (14), where the initial fluid volume of the chamber ($V_f$), the cross sectional area of the chamber (A), the piezoelectric material thickness or height ($l_p$), the piezoelectric modulus ($d_{33}$), and the drive voltage parameter $E_3 = V_{dr}/l_p$ are all known. In some embodiments, the compressibility of the fluid is determined with the fluid being analyzed downhole. In some embodiments, the compressibility of the fluid is determined using an apparatus such as described above with respect to FIGS. 1, 2, and either 6a and 6b or 7a and 7b. In some embodiments, the fluid is a hydrocarbon-containing reservoir fluid. In some embodiments, an indication of the compressibility of the fluid is provided on a log that shows the compressibility as a function of location (e.g. depth) in a formation. The log may be provided and displayed on a computer or other electronic monitor, or may be provided and displayed on a tangible medium such as paper. In some embodiments, compressibility determinations are made for different samples of fluid obtained at different locations downhole, and a log of the fluid compressibility as a function of depth may be provided and displayed.

According to one aspect, the dimensional (and volume) changes in a piezo-ceramic element is sensitive to the make of the piezo-ceramic material. Accurate values for piezoelectric moduli $d_{31}$ and $d_{33}$, are useful for determining $\beta_T$. While current meters have a range of 1 to 2000 pC $N^{-1}$, and the error in $d_{33}$ measurements has been reported to be approximately 2% for 100-2000 pC $N^{-1}$, piezo-ceramic elements can be calibrated for their true piezoelectric coefficients using reference fluid measurements, and any error in compressibility contributed by $d_{33}$ or $d_{31}$ can be eliminated. In addition, the physical setup of the piezoelectric element and the fluid chamber may be calibrated for the variations in piezoelectric coefficients with respect to pressure and temperature in order to maintain measurement accuracy.

In some embodiments, once the compressibility of the fluid is determined (e.g., using equation (12) or (14)), other characteristics of the fluid may be determined using other measurements in conjunction with the determination of compressibility. Thus, by way of example only, the bulk density of the fluid in the chamber may be inferred from a determination of the speed of sound inside the chamber (as determined by a sound velocity sensor) and the compressibility. More particularly, $$v = \sqrt{\partial P/\partial \rho} = \sqrt{(\rho \beta_s)^{-1}} = \sqrt{\rho^{-1} K_s} \quad (15)$$

where the derivative is at constant entropy, and $v$ is the measured speed of sound, P is the pressure, $\rho$ is the density of the fluid, $\beta_s$ is the adiabatic compressibility at constant entropy, and $K_s$ is the bulk modulus. $\beta_s$ is the product of $\beta_T$ and the constant pressure to constant volume specific heat ratio commonly denoted as $\gamma$. If the density of the fluid is measured independently through any of several known mechanism, e.g a vibrating tube, $\beta_s$ can be inferred if the acoustic velocity is known. Thus, from the measured $\beta_T$, $\gamma$ may be determined from $$\gamma = \beta_T/\beta_s. \quad (16)$$

In one aspect, some of methods and processes described above are performed by a processor, such as determining compressibility according to equation (12) or equation (14), or determining bulk density according to equation (15), or specific heat ratio according to equation (16). The term "processor" should not be construed to limit the embodiments disclosed herein to any particular device type or system. The processor may include a computer system. The computer system may also include a computer processor (e.g., a microprocessor, microcontroller, digital signal processor, or general purpose computer) for executing any of the methods and processes described above. The computer system may further include a memory such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCM-CIA card), or other memory device.

The methods and processes described above may be implemented as computer program logic for use with the computer processor. The computer program logic may be embodied in various forms, including a source code form or a computer executable form. Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the computer processor. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

Alternatively or additionally, the processor may include discrete electronic components coupled to a printed circuit board, integrated circuitry (e.g., Application Specific Integrated Circuits (ASIC)), and/or programmable logic devices (e.g., a Field Programmable Gate Arrays (FPGA)). Any of the methods and processes described above can be implemented using such logic devices.

Although only a few examples have been described in detail above, those skilled in the art will readily appreciate that many modifications are possible in the examples without materially departing from this subject disclosure. Thus, by way of example only, and not by way of limitation, while various embodiments describe determining compressibility by decreasing the fluid chamber volume through the use of a piezoelectric element, it is possible to increase the fluid chamber volume using a piezoelectric element and to determine compressibility of the fluid within the fluid chamber. Also, particular arrangements of chambers and piezoelectric materials have been shown, such as a piezoelectric material located inside a container with the fluid, and a piezoelectric material located inside a container but separated from the fluid by a membrane or diaphragm, it will be appreciated that other arrangements could be provided as long as the change in one or more dimensions of the piezoelectric material causes a change in fluid volume inside the chamber. Further, while particular piezoelectric materials were described, and while particular applied voltages were described, it will be appreciated that other materials and other voltages could be used. Accordingly, all such modifications are intended to be included within the scope of this disclosure as defined in the following claims. In the claims, means-plus-function clauses are intended to cover the structures described herein as performing the recited function and not only structural equivalents, but also equivalent structures. It is the express intention of the applicant not to invoke 35 U.S.C. § 112, paragraph 6 for any limitations of any of the claims herein, except for those in which the claim expressly uses the words 'means for' together with an associated function. As used in the description and claims, phrases in the form of "at least one of [a] and [b]" should be construed as being disjunctive, i.e., encompassing arrangements that include [a] but not [b], arrangements that include [b] but not [a], and arrangements that include [a] and [b].

What is claimed is:

1. A method of determining an indication of a fluid parameter, comprising:
    a) providing a rigid chamber and a piezoelectric material that is at least one of (i) within the chamber and (ii) operatively coupled to a wall of the chamber;
    b) introducing the fluid into the chamber;
    c) applying a voltage to the piezoelectric material, thereby changing the volume of the chamber available to the fluid;
    d) measuring an indication of the pressure P in the chamber; and
    e) determining a compressibility of the fluid as a function of a change in pressure in the chamber resulting from the changing of the volume of the chamber available to the fluid.

2. The method according to claim 1, further comprising:
locating the chamber and the piezoelectric material downhole in a borehole that traverses a formation, wherein the fluid is formation fluid, and applying a voltage and measuring an indication are performed while the chamber and the piezoelectric material are located downhole.

3. The method according to claim 2, wherein:
introducing the fluid into the chamber comprises extracting the fluid from the formation.

4. The method according to claim 3, wherein:
the fluid comprises one or more hydrocarbons.

5. The method according to claim 2, wherein:
the piezoelectric material is located in the fluid in the chamber, and
the determination comprises determining the compressibility $\beta_T$ according to $$P = \frac{\alpha(2d_{31} + d_{33})E_3}{\beta_T},$$

where $\Delta P$ is said change in pressure, $\alpha$ is a volume ratio of piezoelectric material to fluid, $d_{31}$ and $d_{33}$ are tensor components of piezoelectric moduli of said piezoelectric material, and $E_3$ is a drive voltage parameter related to said voltage.

6. The method according to claim 5, wherein:
changing the volume of the chamber is controlled such that $\Delta P/P$ is less than 1/100.

7. The method according to claim 2, wherein:
the chamber includes a dividing diaphragm with the piezoelectric material located on a first side of the dividing diaphragm and the fluid located on a second side of the dividing diaphragm, and
the determining the compressibility of the fluid comprises determining the compressibility $\beta_T$ according to $$P = \frac{d_{33}E_3 A l_p}{V_f \beta_T},$$

where $V_f$ is the initial fluid volume before the applying a voltage, A is the cross-sectional area of chamber, $l_p$ is the length of the piezoelectric material when a drive voltage is applied to the piezoelectric material, $d_{33}$ is a tensor component of a piezoelectric modulus along a poling direction of the piezoelectric material, and $E_3$ is a drive voltage parameter related to the voltage.

8. The method according to claim 7, wherein:
changing the volume of the chamber is controlled such that $\Delta P/P$ is less than 1/100.

9. The method according to claim 2, further comprising:
measuring a speed of sound in the fluid;
measuring a bulk density of the fluid; and
determining a specific heat ratio of the fluid.

10. The method according to claim 1, wherein:
the piezoelectric material is a ceramic material.

11. An apparatus for determining an indication of a parameter of a fluid, comprising:
a) a fluid chamber comprising a wall and configured to receive the fluid;
b) a piezoelectric material coupled to the wall of the fluid chamber;
c) a pressure sensor in fluid communication with the fluid chamber, the pressure sensor configured to provide an indication of a pressure in the fluid chamber;
d) a voltage source coupled to the piezoelectric material such that when the voltage source applies a voltage to the piezoelectric material, the piezoelectric material deforms; and
e) a processor coupled to the pressure sensor, the processor configured to determine the compressibility of the fluid as a function of a change in pressure in the chamber resulting from said deformation of said piezoelectric material.

12. The apparatus according to claim 11, wherein:
the apparatus is a borehole apparatus and further comprises a housing, wherein the fluid chamber, piezoelectric material and pressure sensor are located in the housing.

13. The apparatus according to claim 12, further comprising:
a probe extending from the housing and into contact with a wall of a formation, and
a fluid coupler that couples said probe and said fluid chamber.

14. The apparatus according to claim 13, wherein:
the fluid comprises one or more hydrocarbons.

15. The apparatus according to claim 11, wherein:
the piezoelectric material is located in said fluid in the chamber, and
the processor determines the compressibility $\beta_T$ according to $$P = \frac{\alpha(2d_{31} + d_{33})E_3}{\beta_T},$$

where $\Delta P$ is said change in pressure, $\alpha$ is a volume ratio of piezoelectric material to fluid, $d_{31}$ and $d_{33}$ are tensor components of piezoelectric moduli of the piezoelectric material, and $E_3$ is a drive voltage parameter related to a voltage of the voltage source.

16. The apparatus according to claim 11, wherein:
the chamber includes a dividing diaphragm with the piezoelectric material located on a first side of the dividing diaphragm and the fluid located on a second side of the dividing diaphragm, and
the processor is configured to determine the compressibility $\beta_T$ according to $$P = \frac{d_{33}E_3 A l_p}{V_f \beta_T},$$

where $V_f$ is the initial fluid volume before said applying a voltage, A is the cross-sectional area of the chamber, $l_p$ is the thickness of the piezoelectric material in the poling direction, $d_{33}$ is a tensor component of a piezoelectric modulus along a poling direction of the piezoelectric material, and $E_3$ is a drive voltage parameter related to the voltage of the voltage source.

17. The apparatus according to claim 16, wherein:
the piezoelectric material comprises a ceramic element.

18. The apparatus according to claim 16, wherein:
the piezoelectric material comprises a plurality of ceramic elements.

19. The apparatus according to claim 16, wherein:
the dividing diaphragm comprises a metal membrane.

20. The apparatus according to claim 11, further comprising:
a speed-of-sound sensor operatively coupled to the chamber and configured to provide an output to the processor, wherein the processor is configured to determine an indication of at least one of a bulk density and a specific heat of the fluid as a function of the compressibility and a speed of sound within said fluid as determined by the processor.

* * * * *